(12) United States Patent
Hatta et al.

(10) Patent No.: US 12,110,470 B2
(45) Date of Patent: Oct. 8, 2024

(54) PERFLUOROPOLYETHER COMPOUND, LUBRICANT AND MAGNETIC DISK

(71) Applicant: Moresco Corporation, Kobe (JP)

(72) Inventors: Tomomi Hatta, Kobe (JP); Tsuyoshi Shimizu, Kobe (JP)

(73) Assignee: Moresco Corporation, Kobe (JP)

( * ) Notice: Subject to any disclaimer, the term of this patent is extended or adjusted under 35 U.S.C. 154(b) by 15 days.

(21) Appl. No.: 17/620,930

(22) PCT Filed: Jun. 15, 2020

(86) PCT No.: PCT/JP2020/023384
§ 371 (c)(1),
(2) Date: Dec. 20, 2021

(87) PCT Pub. No.: WO2021/002178
PCT Pub. Date: Jan. 7, 2021

(65) Prior Publication Data
US 2022/0372395 A1 Nov. 24, 2022

(30) Foreign Application Priority Data
Jul. 3, 2019 (JP) .................. 2019-124427

(51) Int. Cl.
*C10M 147/04* (2006.01)
*C10M 107/38* (2006.01)
(Continued)

(52) U.S. Cl.
CPC ......... *C10M 147/04* (2013.01); *G11B 5/7257* (2020.08); *C10M 2213/06* (2013.01); *C10N 2040/18* (2013.01)

(58) Field of Classification Search
CPC .............. C10M 105/54; C10M 107/38; C10M 147/04; C10M 2213/06; G11B 5/725; G11B 5/7257; G11B 5/82
See application file for complete search history.

(56) References Cited

U.S. PATENT DOCUMENTS 4,692,378 A * 9/1987 Ishihara ............... G11B 5/7257
428/524
5,512,373 A 4/1996 Ueda et al.
(Continued)

FOREIGN PATENT DOCUMENTS

JP 06-318319 11/1994
JP 08-63739 3/1996
(Continued)

OTHER PUBLICATIONS

International Search Report from PCT Appliction No. PCT/JP2020/023384 dated Sep. 15, 2020.
(Continued)

*Primary Examiner* — Holly Rickman
*Assistant Examiner* — Linda N Chau
(74) *Attorney, Agent, or Firm* — Harness Dickey & Pierce P.L.C.

(57) ABSTRACT

Provided are a magnetic disk and, in particular, a compound which makes it possible to realize a lubricant having excellent heat resistance and solubility in a fluorine-based solvent. A perfluoropolyether compound in accordance with an aspect of the present invention has, in hydrocarbon groups at both terminals thereof, five or six hydroxyl groups in total.

5 Claims, 1 Drawing Sheet

(51) Int. Cl.
    *G11B 5/725*     (2006.01)
    *C10N 40/18*     (2006.01)

(56) References Cited

U.S. PATENT DOCUMENTS

| | | | |
|---|---|---|---|
| 6,638,622 B2* | 10/2003 | Dai | C10M 107/38 |
| 8,679,655 B2* | 3/2014 | Kobayashi | C10M 105/54 |
| | | | 508/579 |
| 8,980,450 B2 | 3/2015 | Kobayashi | |
| 11,332,686 B2* | 5/2022 | Fukumoto | G11B 5/7257 |
| 2005/0282045 A1 | 12/2005 | Sonoda | |
| 2010/0239887 A1 | 9/2010 | Kobayashi | |
| 2012/0002323 A1 | 1/2012 | Kato et al. | |
| 2017/0260472 A1* | 9/2017 | Sagata | C10M 107/38 |
| 2018/0047419 A1* | 2/2018 | Fukumoto | C08G 65/2639 |

FOREIGN PATENT DOCUMENTS

| | | |
|---|---|---|
| JP | 10-149527 | 6/1998 |
| JP | 11-60720 | 3/1999 |
| JP | 11-131083 | 5/1999 |
| JP | 2005-63484 A | 3/2005 |
| JP | 2005-122790 A | 5/2005 |
| JP | 61-99926 A | 9/2017 |
| JP | 61-99926 B2 | 9/2017 |
| JP | 2019019278 A | 2/2019 |
| WO | 2009066784 A1 | 5/2009 |
| WO | 2010106790 A1 | 9/2010 |
| WO | 2016084781 A1 | 6/2016 |

OTHER PUBLICATIONS

Written Opinion from PCT Appliction No. PCT/JP2020/023384 dated Sep. 15, 2020.
Notice of Allowance from U.S. Appl. No. 12/734,699 dated Nov. 7, 2013.
Office Action from U.S. Appl. No. 12/734,699 dated Apr. 26, 2013.
Restriction Requirement from U.S. Appl. No. 12/734,699 dated Jul. 6, 2012.
Kasai, P., "Perfluoropolyethers: Intramolecular Disproportionation," Macromolecules, 25: 6791-6799 (1992).
Office Action from U.S. Appl. No. 12/734,699 dated Oct. 22, 2012.
International Search Report from PCT Application No. PCT/JP2008/071281 dated Jan. 13, 2009.

* cited by examiner

PERFLUOROPOLYETHER COMPOUND, LUBRICANT AND MAGNETIC DISK

TECHNICAL FIELD

The present invention relates to a perfluoropolyether compound, a lubricant, and a magnetic disk.

BACKGROUND ART

Many of existing magnetic disks are each constituted by: a recording layer disposed on a substrate; a protective layer disposed on the recording layer in order to protect information recorded on the recording layer; and a lubricant layer disposed on the protective layer. For lubricant layers of recent magnetic disks, lubricants having a lowered molecular weight are used so as to cause the lubricant layers to be thinner films. As a conventional technique concerning surface lubricants for magnetic disks, the technique disclosed in Patent Literature 1 is, for example, known. Patent Literature 1 discloses various perfluoropolyether compounds.

CITATION LIST

Patent Literature

[Patent Literature 1]
International Publication No. WO 2009/066784

SUMMARY OF INVENTION

Technical Problem

A lubricant having a lowered molecular weight tends to easily volatilize. In a case where the lubricant disappears by volatilizing, abrasion is likely to occur when a magnetic disk and a magnetic head contact with each other. And also impurities are likely to adhere to the magnetic disk. Therefore, a lubricant having low volatility, i.e., excellent heat resistance is required.

However, the conventional technique as described above still have room for improvement, from the viewpoint of lowering the volatility of a lubricant, i.e., realizing a lubricant having excellent heat resistance and excellent solubility in a fluorine-based solvent.

An object of an aspect of the present invention is to provide a compound which makes it possible to realize a lubricant having excellent heat resistance and favorable solubility in a fluorine-based solvent.

Solution to Problem

As a result of conducting diligent studies in order to attain the above object, the inventors of the present invention found that a perfluoropolyether compound having, in hydrocarbon groups at both terminals thereof, five or six hydroxyl groups in total has excellent heat resistance and exhibits favorable solubility in a fluorine-based solvent, thereby completing the present invention. That is, the present invention includes the following aspects.

<1> A perfluoropolyether compound represented by the following formula (1):

$$R^1—CH_2—R^2—CH_2—R^3 \quad (1)$$

wherein: $R^1$ is $HOCH_2CH(OH)CH_2OCH_2CH(OH)CH_2O—$;

wherein x is a real number of 0 to 3, y is a real number of 0 to 1, z, l, m, n, and o are each independently a real number of 0 to 15, and any one of x and y is a real number of 1 or more and at least any one of z, l, m, n, and o is a real number of 1 or more; and $R^3$ is $—OCH_2CH(OH)CH_2OH$ or $—OCH_2CH(OH)CH_2OCH_2CH(OH)CH_2OH$.

<2> A lubricant including a perfluoropolyether compound described in <1>.

<3> A magnetic disk including: a recording layer; a protective layer disposed on the recording layer; and a lubricant layer disposed on the protective layer, the lubricant layer containing a lubricant described in <2>.

Advantageous Effects of Invention

According to an aspect of the present invention, it is possible to provide a compound which makes it possible to realize a lubricant having excellent heat resistance and having favorable solubility in a fluorine-based solvent.

DESCRIPTION OF EMBODIMENTS

Figure 1:
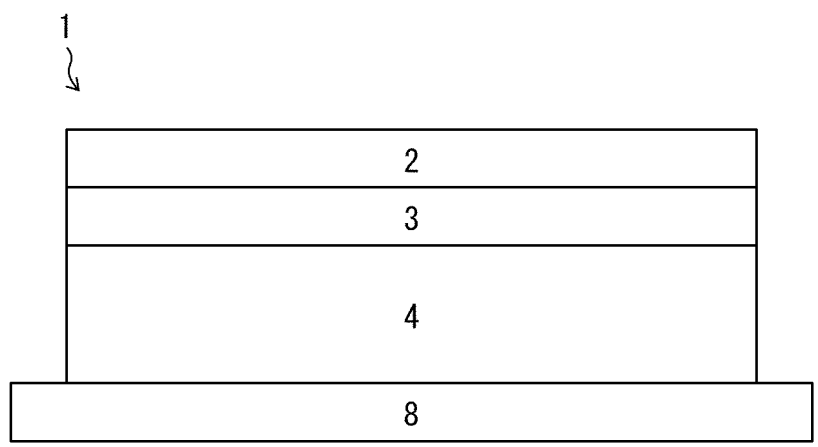
FIG. 1 is a cross-sectional view illustrating a configuration of a magnetic disk in accordance with an embodiment of the present invention.

The following description will discuss embodiments of the present invention in detail. Note, however, that the present invention is not limited to the embodiments, but can be altered within this disclosure. The present invention also encompasses, in its technical scope, any embodiment derived by combining technical means disclosed in differing embodiments. Note that the expression "A to B", representing a numerical range, herein means "not less than A but not more than B" unless otherwise specified in this specification.

[1. Perfluoropolyether Compound]

A perfluoropolyether compound in accordance with an embodiment of the present invention has a structure represented by the following formula (1):

$$R^1—CH_2—R^2—CH_2—R^3 \quad (1)$$

wherein: $R^1$ is $HOCH_2CH(OH)CH_2OCH_2CH(OH)CH_2O—$;

wherein x is a real number of 0 to 3, y is a real number of 0 to 1, z, l, m, n, and o are each independently a real number of 0 to 15, and any one of x and y is a real number of 1 or more and at least any one of z, l, m, n, and o is a real number of 1 or more; and $R^3$ is $—OCH_2CH(OH)CH_2OH$ or $—OCH_2CH(OH)CH_2OCH_2CH(OH)CH_2OH$.

The inventors of the present invention devised various synthetic pathways, in order to develop a lubricant having more excellent heat resistance and having more excellent solubility in a fluorine-based solvent, than existing lubricants. As a result, the inventors of the present invention found that a perfluoropolyether compound which is controlled so that the number of hydroxyl groups at both terminals thereof is five or six in total has excellent heat resistance and has favorable solubility in a fluorine-based solvent. In a high-temperature environment, the lubricant applied to a magnetic disk allows a lubricant layer to be small in amount of weight reduction, and is hard to volatilize. Thus, the lubricant exhibits excellent heat resistance.

The inventors of the present invention also found that a perfluoropolyether compound in which the number of hydroxyl groups at both terminals thereof is seven or more in total has poor solubility in a fluorine-based solvent.

In this specification, whether a lubricant has "excellent heat resistance" can be evaluated by carrying out (i) evaluation of heat resistance by thermogravimetry (TG) and (ii) evaluation of evaporativity on a magnetic disk, each of which is described in Examples. The evaluation of heat resistance by TG evaluates how high a 50% weight reduction temperature (T50) of a lubricant layer, obtained by applying a lubricant to a magnetic disk, after the magnetic disk is heated is. The evaluation of evaporativity on a magnetic disk evaluates how low a thickness reduction rate of a lubricant layer, obtained by applying a lubricant to a magnetic disk, after the magnetic disk is heated is. In this specification, whether a lubricant has "favorable solubility in a fluorine-based solvent" can be evaluated by evaluation of solubility in a fluorine-based solvent described in Examples.

The perfluoropolyether compound in accordance with an embodiment of the present invention is not limited to any particular one, provided that the perfluoropolyether compound is represented by the foregoing formula (1). The perfluoropolyether compound contains any combination of $R^1$ to $R^3$ described above.

Examples of $R^2$ include a Demnum skeleton: $-CF_2CF_2O-(CF_2CF_2CF_2O)_m CF_2CF_2-$, a Fomblin skeleton: $-CF_2O-(CF_2O)_z(CF_2CF_2O)_l CF_2-$, a C2 skeleton: $-CF_2O-(CF_2CF_2O)_l CF_2-$, a C4 skeleton: $-CF_2CF_2CF_2O-(CF_2CF_2CF_2CF_2O)_n CF_2CF_2CF_2-$, and a Krytox skeleton: $-CF(CF_3)O-(CF(CF_3)CF_2O)_o CF(CF_3)-$. $R^2$ is preferably the Demnum skeleton. $R^2$ may be a skeleton constituted by only one of the above skeletons or may be alternatively a skeleton constituted by two or more of the above skeletons. The skeleton constituted by two or more of the above skeletons is not limited to any particular one, and may be, for example, a skeleton constituted by the Krytox skeleton and the C2 skeleton. In the above skeletons, z, l, m, n, and o are each independently a real number of 1 to 15. Note that in the Fomblin skeleton, $CF_2O$ and $CF_2CF_2O$ can be randomly repeated.

[2. Method of Producing Perfluoropolyether Compound]

A method of producing the perfluoropolyether compound in accordance with an Example of the present invention is not limited to any particular one. The perfluoropolyether compound can be obtained, for example, by reacting a linear fluoropolyether (a) having a hydroxyl group(s) at a terminal(s) thereof, glycidol, 2,2-dimethyl-4-(2,3-epoxy) propoxymethyl-1,3-dioxolane, 3-(2-oxiranylmethoxy)-1,2-propanediol, and/or the like.

For example, in a case where the perfluoropolyether compound which has the Demnum skeleton is obtained, the linear fluoropolyether (a) having a hydroxyl group(s) at a terminal(s) thereof is, for example, a compound represented by $HOCH_2-CF_2CF_2O-(CF_2CF_2CF_2O)_v CF_2CF_2-CH_2OH$. The number average molecular weight of this linear fluoropolyether is preferably 500 to 4000, and more preferably 800 to 2000. Note, here, that the number average molecular weight is a value measured by $^{19}F$-NMR with use of JNM-ECX400 available from JEOL Ltd. In the NMR measurement, a sample is used as a neat solution without being diluted with a solvent. A known peak that indicates a part of a skeleton structure of fluoropolyether is used as a reference for a chemical shift. Note that v is a real number of 1 to 15, and preferably a real number of 3 to 12. In a case where v is a real number of 3 to 12, the molecular chain becomes flatter. Thus, it is preferable that v be a real number of 3 to 12.

Note that in a case where the perfluoropolyether compound which has a skeleton other than the Demnum skeleton is obtained, a linear fluoropolyether having a desired skeleton and having a hydroxyl group(s) at a terminal(s) thereof can be similarly used.

The linear fluoropolyether (a) is a compound having a molecular weight distribution, and has a molecular weight distribution (PD), represented by weight average molecular weight/number average molecular weight, of preferably 1.0 to 1.5, more preferably 1.0 to 1.3, and even more preferably 1.0 to 1.1. Note that the molecular weight distribution is a property value obtained with use of HPLC-8220GPC available from Tosoh Corporation, a column (PLgel Mixed E) available from Polymer Laboratories, an HCFC-based substitute for CFCs as an eluent, and a non-functional perfluoropolyether as a reference substance.

The perfluoropolyether compound in accordance with an embodiment of the present invention can be synthesized, specifically, by the following method. First, the linear fluoropolyether (a) having a hydroxyl group(s) at a terminal(s) thereof, glycidol, and/or the like are reacted with each other in the presence of a catalyst. A reaction temperature is 20° C. to 90° C., and preferably 60° C. to 80° C. A reaction time is 5 hours to 20 hours, and preferably 10 hours to 18 hours. The glycidol and/or the like are/is preferably used in an amount of 1 equivalent to 3 equivalents with respect to (a), and the catalyst is preferably used in an amount of 0.01 equivalents to 0.5 equivalents with respect to (a). As the catalyst, an alkaline compound such as sodium t-butoxide or potassium t-butoxide can be used. The reaction may be carried out in a solvent. Examples of the solvent include t-butyl alcohol, toluene, and xylene. Thereafter, a resulting reaction product is refined, for example, by water washing or silica gel column chromatography. As a result, the perfluoropolyether compound represented by the foregoing formula (1) is obtained.

[3. Lubricant]

A lubricant in accordance with an embodiment of the present invention contains the perfluoropolyether compound in accordance with an embodiment of the present invention. The perfluoropolyether compound can be also used alone as the lubricant. Alternatively, the perfluoropolyether compound and any other component which are mixed at an arbitrary ratio may be used as the lubricant, provided that the performance of the lubricant is not impaired.

Examples of the any other component include: known lubricants for magnetic disks, such as Fomblin (registered trademark) Zdol (available from Solvay Solexis), Ztetraol (available from Solvay Solexis), Demnum (registered trademark) (available from Daikin Industries, Ltd.), and Krytox (registered trademark) (available from DuPont); MORESCO PHOSFAROL A20H (available from MORESCO Corporation); and MORESCO PHOSFAROL D-4OH (available from MORESCO Corporation).

The lubricant can be used as a lubricant for recording media, in order to improve the sliding properties of magnetic disks. The lubricant can also be used as a lubricant for recording media (e.g., magnetic tapes) other than magnetic disks, in recording devices that involve sliding between the recording media and heads. The lubricant can also be used as a lubricant for other apparatuses which have parts that involve sliding, not confined to the recording devices.

[4. Magnetic Disk]

A magnetic disk 1 in accordance with an embodiment of the present invention includes, as illustrated in FIG. 1, a recording layer 4, a protective film layer (protective layer) 3, and a lubricant layer 2, which are disposed on a non-magnetic substrate 8. The lubricant layer 2 contains the foregoing lubricant.

Figure 2:
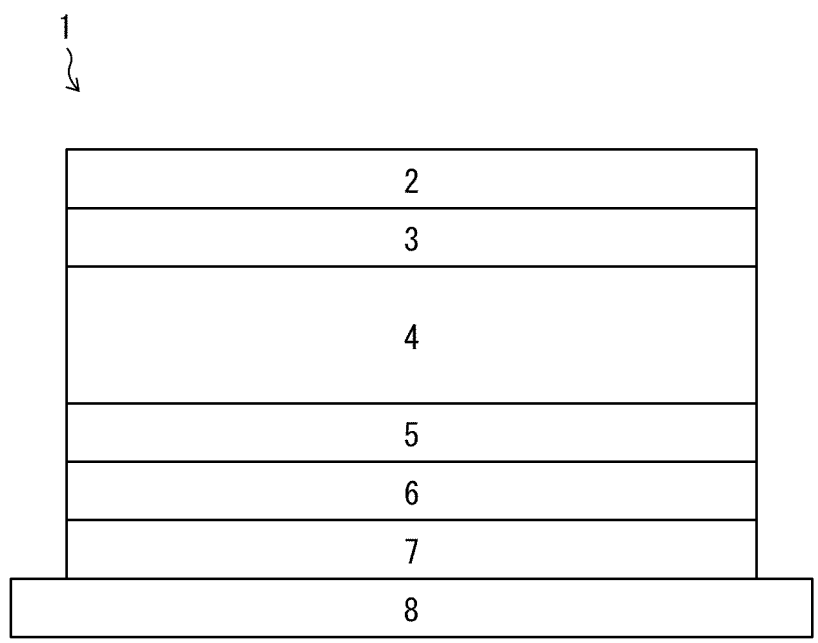
FIG. 2 is a cross-sectional view illustrating a configuration of a magnetic disk in accordance with an embodiment of the present invention.

In an embodiment, the magnetic disk can include, like a magnetic disk 1 illustrated in FIG. 2, a lower layer 5 that underlies the recording layer 4, one or more soft magnetic lower layers 6 that underlie the lower layer 5, and an adhesive layer 7 that underlies the one or more soft magnetic lower layers 6. In an embodiment, all these layers can be formed on the non-magnetic substrate 8.

Each of the layers of the magnetic disk 1, other than the lubricant layer 2, can contain a material that is known in this technical field to be suitable for a corresponding one of layers of a magnetic disk. Examples of the material of the recording layer 4 include: an alloy of an element (e.g., iron, cobalt, and nickel) from which a ferromagnetic material can be formed and chromium, platinum, tantalum or the like; and an oxide of the alloy. Examples of the material of the protective layer 3 include carbon, $Si_3N_4$, SiC, and $SiO_2$. Examples of the material of the non-magnetic substrate 8 include an aluminum alloy, glass, and polycarbonate.

[5. Method of Producing Magnetic Disk]

A method of producing the magnetic disk in accordance with an aspect of the present invention includes a step of forming a lubricant layer by placing the lubricant in accordance with an embodiment of the present invention on an exposed surface of a protective layer of a stack of a recording layer and the protective layer.

There is no particular limitation on a method of forming the lubricant layer by placing the lubricant on the exposed surface of the protective layer of the stack of the recording layer and the protective layer. It is preferable that the lubricant be placed on the exposed surface of the protective layer by the following method: the lubricant is diluted with a solvent and then placed on the exposed surface. Examples of the solvent include: PF-5060, PF-5080, HFE-7100, and HFE-7200 available from 3M; and Vertrel-XF (registered trademark) available from DuPont. The lubricant diluted with the solvent has a concentration of preferably 0.001 wt % to 1 wt %, more preferably 0.005 wt % to 0.5 wt %, and even more preferably 0.01 wt % to 0.1 wt %. In a case where the concentration of the lubricant diluted with the solvent is 0.01 wt % to 0.1 wt %, the viscosity of the lubricant is low enough to easily control the thickness of the lubricant layer.

The following method may be employed: the recording layer and the protective layer are formed in this order; the lubricant is placed on the exposed surface of the protective layer; and then ultraviolet irradiation or heat treatment is carried out.

The ultraviolet irradiation or heat treatment can form stronger bonds between the lubricant layer and the exposed surface of the protective layer and, in turn, prevent the lubricant from evaporating from heat. In a case where the ultraviolet irradiation is carried out, it is preferable to use an ultraviolet ray having a wavelength of 185 nm or 254 nm as the dominant wavelength, in order to activate the exposed surface without affecting deep areas of the lubricant layer and the protective layer. The temperature of the heat treatment is preferably 60° C. to 170° C., more preferably 80° C. to 170° C., and even more preferably 80° C. to 150° C.

EXAMPLES

The present invention will be described below in more detail with reference to Examples. Note, however, that the present invention is not limited to such Examples. Note that evaluation of heat resistance by TG, evaluation of solubility in a fluorine-based solvent, and evaluation of evaporativity on a magnetic disk in Examples below were carried out by the following methods.

[Evaluation of Heat Resistance by TG]

The heat resistance of each of lubricants was evaluated by a thermogravimetric analyzer (EXSTAR6000, available from Seiko Instruments Inc.). 5 mg of each of compounds 1 to 12 was weighed out, and introduced into a container made of platinum. The container was then heated to 550° C. at a rate of temperature rise of 2° C./min under a nitrogen atmosphere. A 50% weight reduction temperature (T50) of each of the compounds was measured. In a case where the 50% weight reduction temperature (T50) was higher than 280° C., the heat resistance was determined as "good". Otherwise, the heat resistance was determined as "poor".

[Evaluation of Solubility in Fluorine-Based Solvent]

0.03 g of each of the compounds 1 to 12 was weighed out, and Asahiklin AK-225G available from AGC Inc. was added thereto so that a resulting solution weighed 30 g. After the solution was stirred hard, the resulting solution was visually checked. In a case where the lubricant dissolved, solubility was determined as "good". In a case where the lubricant did not dissolve, the solubility was determined as "poor".

[Evaluation of Evaporativity on Magnetic Disk]

Each of the compounds 1 to 11 was dissolved in Vertrel-XF available from Chemours-Mitsui Fluoroproduct Co., Ltd., and a resulting solution was applied to a magnetic disk by a dip method so that a lubricant layer would have a thickness of 13 Å. The thickness of the lubricant layer was measured by FT-IR (VERTEX70, available from Bruker). The magnetic disk with the lubricant applied thereto was heated in an oven at 60° C. for a day, and the thickness of the lubricant layer after the heating was measured. In a case where a thickness reduction rate of the lubricant layer after the heating was less than 10%, evaporativity was determined as "good". Otherwise, the evaporativity was determined as "poor".

Note that since the compound 12 was insoluble in Vertrel-XF, it was impossible to apply the compound 12 to a disk.

Example 1

The compound 1, represented by the following formula, was synthesized as below.

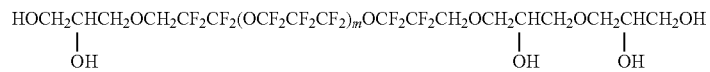

Note that the compound 1 corresponds to a compound represented by formula (1) wherein $R^2$ is a Demnum skeleton and $R^3$ is a hydrocarbon group represented by —OCH$_2$CH(OH)CH$_2$OH.

First, 65 g of t-butyl alcohol, 150 g of per represented by HOCH$_2$CF$_2$CF$_2$O(CF$_2$CF$_2$CF$_2$O)$_m$CF$_2$CF$_2$CH$_2$OH, 1.6 g of potassium t-butoxide, and 9.7 g of glycidol were introduced into a flask, and stirred at 70° C. for 20 hours under an argon atmosphere. Thereafter, a resulting reaction product was washed with water, dehydrated, and then refined with a silica gel chromatograph to obtain 65 g of perfluoropolyether having one hydroxyl group at one terminal thereof and two hydroxyl groups at the other terminal thereof as a result of a reaction with the glycidol.

10 g of this perfluoropolyether compound was dissolved in 5 g t-butyl alcohol. Subsequently, 0.1 g of potassium t-butoxide and 1.8 g of 2,2-dimethyl-4-(2,3-epoxy) propoxymethyl-1,3-dioxolane were added to this solution, and the resulting solution was stirred at 70° C. for hours under an argon atmosphere. Thereafter, a resulting reaction product was washed with water and dehydrated. Then, 100 g of methanol, 11 g of water, and 0.4 g of a 60% nitric acid aqueous solution were added to the reaction product, and a resulting solution was stirred for 39 hours. Thereafter, a resulting reaction product was washed with water, dehydrated, and then refined by distillation to obtain 7 g of the compound 1. Identification results of the compound 1 by NMR are shown below.

$^{19}$F-NMR (solvent: none, reference substance: —OCF$_2$CF$_2$CF$_2$O— in the product was regarded as −129.7 ppm)

δ=−129.7 ppm [11F, —OCF$_2$CF$_2$CF$_2$O—]

δ=−84.1 ppm [22F, —OCF$_2$CF$_2$CF$_2$O—]

δ=−124.0 ppm [4F, —OCF$_2$CF$_2$CH$_2$OCH$_2$CH(OH)CH$_2$OCH$_2$CH(OH)CH$_2$OH, —OCF$_2$CF$_2$CH$_2$OCH$_2$CH(OH)CH$_2$OH]

δ=−86.4 ppm [4F, —OCF$_2$CF$_2$CH$_2$OCH$_2$CH(OH)CH$_2$OCH$_2$CH(OH)CH$_2$OH, —OCF$_2$CF$_2$CH$_2$OCH$_2$CH(OH)CH$_2$OH]

As a result of $^{19}$F-NMR, it was found that, in the compound 1, m=5.7.

$^1$H-NMR (solvent: none, reference substance: D$_2$O)

δ=3.0 ppm to 4.4 ppm [19H, HOCH$_2$CH(OH)CH$_2$OCH$_2$CF$_2$CF$_2$O(CF$_2$CF$_2$CF$_2$O)$_m$CF$_2$CF$_2$CH$_2$O CH$_2$CH(OH)CH$_2$OCH$_2$CH(OH)CH$_2$OH]

δ=4.6 ppm [5H, HOCH$_2$CH(OH)CH$_2$OCH$_2$CF$_2$CF$_2$O (CF$_2$CF$_2$CF$_2$O)$_m$CF$_2$CF$_2$CH$_2$O CH$_2$CH(OH)CH$_2$OCH$_2$CH(OH)CH$_2$OH]

The resulting compound 1 was used as a lubricant in Example 1.

Example 2

The compound 2, represented by the following formula, was synthesized as below.

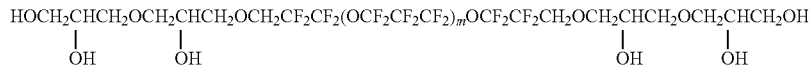

Note that the compound 2 corresponds to a compound represented by formula (1) wherein $R^2$ is a Demnum skeleton and $R^3$ is a hydrocarbon group represented by —OCH$_2$CH(OH)CH$_2$OCH$_2$CH(OH)CH$_2$OH.

First, 65 g of t-butyl alcohol, 25 g of perfluoropolyether represented by HOCH$_2$CF$_2$CF$_2$O(CF$_2$CF$_2$CF$_2$O)$_m$CF$_2$CF$_2$CH$_2$OH, 0.3 g of potassium t-butoxide, and 9.6 g of 2,2-dimethyl-4-(2,3-epoxy)propoxymethyl-1,3-dioxolane were introduced into a flask, and stirred at 70° C. for 23 hours under an argon atmosphere. Thereafter, a resulting reaction product was washed with water and dehydrated. Then, 100 g of methanol, 11 g of water, and 0.4 g of a 60% nitric acid aqueous solution were added to the reaction product, and a resulting solution was stirred for 39 hours. Thereafter, a resulting reaction product was washed with water, dehydrated, and then refined by distillation to obtain 20 g of the compound 2. Identification results of the compound 2 by NMR are shown below.

$^{19}$F-NMR (solvent: none, reference substance: —OCF$_2$CF$_2$CF$_2$O— in the product was regarded as −129.7 ppm)

δ=−129.7 ppm [11F, —OCF$_2$CF$_2$CF$_2$O—]

δ=−84.1 ppm [22F, —OCF$_2$CF$_2$CF$_2$O—]

δ=−124.0 ppm [4F, —OCF$_2$CF$_2$CH$_2$O CH$_2$CH(OH) CH$_2$O CH$_2$(OH)CH$_2$OH, —OCF$_2$CF$_2$CH$_2$OCH$_2$CH(OH)CH$_2$OH]

δ=−86.4 ppm [4F, —OCF$_2$CF$_2$CH$_2$OCH$_2$CH(OH)CH$_2$OCH$_2$CH(OH)CH$_2$OH, —OCF$_2$CF$_2$CH$_2$OCH$_2$CH(OH)CH$_2$OH]

As a result of $^{19}$F-NMR, it was found that, in the compound 2, m=5.5.

$^1$H-NMR (solvent: none, reference substance: D$_2$O)

δ=3.0 ppm to 4.4 ppm [24H, HOCH$_2$CH(OH)CH$_2$OCH$_2$CH(OH)CH$_2$OCH$_2$CF$_2$CF$_2$O(CF$_2$CF$_2$CF$_2$O)$_m$CF$_2$CF$_2$CH$_2$OCH$_2$CH(OH)CH$_2$OCH$_2$CH(OH)CH$_2$OH]

δ=4.6 ppm [6H, HOCH$_2$CH(OH)CH$_2$OCH$_2$CH(OH)CH$_2$OCH$_2$CF$_2$CF$_2$O(CF$_2$CF$_2$CF$_2$O)$_m$CF$_2$CF$_2$CH$_2$OCH$_2$CH(OH)CH$_2$OCH$_2$CH(OH)CH$_2$OH]

The resulting compound 2 was used as a lubricant in Example 2.

Example 3

The compound 3, represented by the following formula, was synthesized as below.

HOCH$_2$CHCH$_2$OCH$_2$CF$_2$O(CF$_2$O)$_2$(CF$_2$CF$_2$O)$_x$CF$_2$CH$_2$OCH$_2$CHCH$_2$OCH$_2$CHCH$_2$OH
       |                                                       |                    |
      OH                                               OH               OH

Note that the compound 3 corresponds to a compound represented by formula (1) wherein R$^2$ is a Fomblin skeleton and R$^3$ is a hydrocarbon group represented by —OCH$_2$CH(OH)CH$_2$OH.

The compound 3 was synthesized in the same manner as the compound 1, except that perfluoropolyether to be used was changed to perfluoropolyether represented by HOCH$_2$CF$_2$O(CF$_2$O)$_z$(CF$_2$CF$_2$O)$_l$CF$_2$CH$_2$OH. Identification results of the compound 3 by NMR are shown below.

$^{19}$F-NMR (solvent: none, reference: —OCF$_2$OCF$_2$CF$_2$OCF$_2$— in the product was regarded as −90.7 ppm)

δ=−52.1 ppm, −53.7 ppm, −55.4 ppm [11F, —OCF$_2$O—]
δ=−89.1 ppm, −90.7 ppm [23F, —OCF$_2$CF$_2$O—]
δ=−77.9 ppm, −80.0 ppm [4F, —OCF$_2$CH$_2$O—]

As a result of $^{19}$F-NMR, it was found that, in the compound 3, z=5.6 and l=5.7.

$^1$H-NMR (solvent: none, reference substance: D$_2$O)

δ=3.0 ppm to 4.4 ppm [19H, HOCH$_2$CH(OH)CH$_2$OCH$_2$CF$_2$O(CF$_2$O)$_o$(CF$_2$CF$_2$O)$_l$CF$_2$CH$_2$OCH$_2$CH(OH)CH$_2$OCH$_2$CH(OH)CH$_2$OH]

δ=4.6 ppm [5H, HOCH$_2$CH(OH)CH$_2$OCH$_2$CF$_2$O(CF$_2$O)$_z$(CF$_2$CF$_2$O)$_l$CF$_2$CH$_2$OCH$_2$CH(OH)CH$_2$OCH$_2$CH(OH)CH$_2$OH]

The resulting compound 3 was used as a lubricant in Example 3.

Example 4

The compound 4, represented by the following formula, was synthesized as below.

HOCH$_2$CHCH$_2$OCH$_2$CHCH$_2$OCH$_2$CF$_2$O(CF$_2$O)$_z$(CF$_2$CF$_2$O)$_l$CF$_2$CH$_2$OCH$_2$CHCH$_2$OCH$_2$CHCH$_2$OH
      |          |                                                           |          |
    OH      OH                                                    OH     OH

Note that the compound 4 corresponds to a compound represented by formula (1) wherein R$^2$ is a Fomblin skeleton and R$^3$ is a hydrocarbon group represented by —OCH$_2$CH(OH)CH$_2$OCH$_2$CH(OH)CH$_2$OH.

The compound 4 was synthesized in the same manner as the compound 2, except that perfluoropolyether to be used was changed to perfluoropolyether represented by HOCH$_2$CF$_2$O(CF$_2$O)$_z$(CF$_2$CF$_2$O)$_l$CF$_2$CH$_2$OH. Identification results of the compound 4 by NMR are shown below.

$^{19}$F-NMR (solvent: none, reference: —OCF$_2$OCF$_2$CF$_2$OCF$_2$— in the product was regarded as −90.7 ppm)

δ=−52.1 ppm, −53.7 ppm, −55.4 ppm [11F, —OCF$_2$O—]
δ=−89.1 ppm, −90.7 ppm [23F, —OCF$_2$CF$_2$O—]
δ=−77.9 ppm, −80.0 ppm [4F, —OCF$_2$CH$_2$O—]

As a result of $^{19}$F-NMR, it was found that, in the compound 4, z=5.7 and l=5.8.

$^1$H-NMR (solvent: none, reference substance: D$_2$O)

δ=3.0 ppm to 4.4 ppm [24H, HOCH$_2$CH(OH)CH$_2$OCH$_2$CH(OH)CH$_2$OCH$_2$CF$_2$O(CF$_2$O)$_o$(CF$_2$CF$_2$O)$_l$CF$_2$CH$_2$OCH$_2$CH(OH)CH$_2$OCH$_2$CH(OH)CH$_2$OH]

δ=4.6 ppm [6H, HOCH$_2$CH(OH)CH$_2$OCH$_2$CH(OH)CH$_2$OCH$_2$CF$_2$O(CF$_2$O)$_z$(CF$_2$CF$_2$O)$_l$CF$_2$CH$_2$OCH$_2$CH(OH)CH$_2$OCH$_2$CH(OH)CH$_2$OH]

The resulting compound 4 was used as a lubricant in Example 4.

Example 5

The compound 5, represented by the following formula, was synthesized as below.

HOCH$_2$CHCH$_2$OCH$_2$CF$_2$O(CF$_2$CF$_2$O)$_l$CF$_2$CH$_2$OCH$_2$CHCH$_2$OCH$_2$CHCH$_2$OH
       |                                                      |         |
      OH                                               OH     OH

Note that the compound 5 corresponds to a compound represented by formula (1) wherein R$^2$ is a C2 skeleton and R$^3$ is a hydrocarbon group represented by OCH$_2$CH(OH)CH$_2$OH.

The compound 5 was synthesized in the same manner as the compound 1, except that perfluoropolyether to be used was changed to perfluoropolyether represented by HOCH$_2$CF$_2$O(CF$_2$CF$_2$O)$_l$CF$_2$CH$_2$OH. Identification results of the compound 5 by NMR are shown below.

$^{19}$F-NMR (solvent: none, reference: —OCF$_2$CF$_2$O— in the product was regarded as −90.7 ppm)

δ=−90.7 ppm [47F, —CF$_2$CF$_2$O—]
δ=−79.8 ppm [4F, —CH$_2$CF$_2$O—]

As a result of $^{19}$F-NMR, it was found that, in the compound 5, l=11.8.

¹H-NMR (solvent: none, reference substance: $D_2O$)
δ=3.0 ppm to 4.4 ppm [19H, $HOCH_2CH(OH)$
$CH_2OCH_2CF_2O(CF_2CF_2O)_lCF_2CH_2OCH_2CH(OH)$
$CH_2OCH_2CH(OH)CH_2OH$]
δ=4.6 ppm [5H, $HOCH_2CH(OH)CH_2OCH_2CF_2O$
$(CF_2CF_2O)_lCF_2CH_2OCH_2CH(OH)$ $CH_2OCH_2CH(OH)$
$CH_2OH$]

The resulting compound 5 was used as a lubricant in Example 5.

Example 6

The compound 6, represented by the following formula, was synthesized as below.

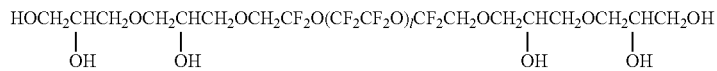

Note that the compound 6 corresponds to a compound represented by formula (1) wherein $R^2$ is a C2 skeleton and $R^3$ is a hydrocarbon group represented by $OCH_2CH(OH)$ $CH_2OCH_2CH(OH)CH_2OH$.

The compound 6 was synthesized in the same manner as the compound 2, except that perfluoropolyether to be used was changed to perfluoropolyether represented by $HOCH_2CF_2O(CF_2CF_2O)_lCF_2CH_2OH$. Identification results of the compound 6 by NMR are shown below.

¹⁹F-NMR (solvent: none, reference: —$OCF_2CF_2O$— in the product was regarded as −90.7 ppm)
δ=−90.7 ppm [34F, —$CF_2CF_2O$—]
δ=−79.8 ppm [4F, —$CH_2CF_2O$—]
As a result of ¹⁹F-NMR, it was found that, in the compound 6, l=8.6.

¹H-NMR (solvent: none, reference substance: $D_2O$)
δ=3.0 ppm to 4.4 ppm [24H, $HOCH_2CH(OH)CH_2OCH_2CH$
$(OH)CH_2OCH_2CF_2O(CF_2CF_2O)_lCF_2CH_2OCH_2CH(OH)$
$CH_2OCH_2CH(OH)CH_2OH$]

δ=4.6 ppm [6H, $HOCH_2CH(OH)CH_2OCH_2CH(OH)$
$CH_2OCH_2CF_2O(CF_2CF_2O)_lCF_2CH_2OCH_2CH(OH)$
$CH_2OCH_2CH(OH)CH_2OH$]

The resulting compound 6 was used as a lubricant in Example 6.

Example 7

The compound 7, represented by the following formula, was synthesized as below.

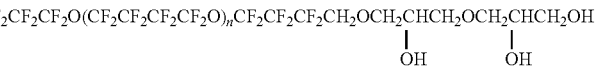

Note that the compound 7 corresponds to a compound represented by formula (1) wherein $R^2$ is a C4 skeleton and $R^3$ is a hydrocarbon group represented by $OCH_2CH(OH)$ $CH_2OH$.

The compound 7 was synthesized in the same manner as the compound 1, except that perfluoropolyether to be used was changed to perfluoropolyether represented by $HOCH_2CF_2CF_2CF_2O(CF_2CF_2CF_2CF_2O)_n$ $CF_2CF_2CF_2CH_2OH$. Identification results of the compound 7 by NMR are shown below.

¹⁹F-NMR (solvent: none, reference: —$OCF_2CF_2CF_2CF_2O$— in the product was regarded as −126.2 ppm)
δ=−127.3 ppm [4F, —$OCF_2CF_2CF_2CH_2O$—]
δ=−126.2 ppm [15F, —$OCF_2CF_2CF_2CF_2O$—]
δ=−120.5 ppm [4F, —$OCF_2CF_2CF_2CH_2O$—]
δ=−83.8 ppm [4F, —$OCF_2CF_2CF_2CF_2O$—, —$OCF_2CF_2CF_2CH_2O$—]

As a result of ¹⁹F-NMR, it was found that, in the compound 7, n=3.7.

¹H-NMR (solvent: none, reference substance: $D_2O$)
δ=3.0 ppm to 4.4 ppm [19H, $HOCH_2CH(OH)$
$CH_2OCH_2CF_2CF_2CF_2O(CF_2CF_2CF_2CF_2O)_n$
$CF_2CF_2CF_2CH_2OCH_2CH(OH)CH_2OCH_2CH(OH)CH_2OH$]

δ=4.6 ppm [5H, $HOCH_2CH(OH)CH_2OCH_2CF_2CF_2CF_2O$
$(CF_2CF_2CF_2CF_2O)_nCF_2CF_2CF_2CH_2OCH_2CH(OH)$
$CH_2OCH_2CH(OH)CH_2OH$]

The resulting compound 7 was used as a lubricant in Example 7.

Example 8

The compound 8, represented by the following formula, was synthesized as below.

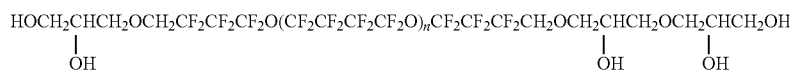

Note that the compound 8 corresponds to a compound represented by formula (1) wherein $R^2$ is a C4 skeleton and $R^3$ is a hydrocarbon group represented by $OCH_2CH(OH)$ $CH_2OCH_2CH(OH)CH_2OH$.

The compound 8 was synthesized in the same manner as the compound 2, except that perfluoropolyether to be used was changed to perfluoropolyether represented by $HOCH_2CF_2CF_2CF_2O(CF_2CF_2CF_2CF_2O)_n$ $CF_2CF_2CF_2CH_2OH$. Identification results of the compound 8 by NMR are shown below.

$^{19}$F-NMR (solvent: none, reference: —OCF$_2$CF$_2$CF$_2$CF$_2$O— in the product was regarded as −126.2 ppm)

δ=−127.3 ppm [4F, —OCF$_2$CF$_2$CF$_2$CH$_2$O—]
δ=−126.2 ppm [15F, —OCF$_2$CF$_2$CF$_2$CF$_2$O—]
δ=−120.5 ppm [4F, —OCF$_2$CF$_2$CF$_2$CH$_2$O—]
δ=−83.8 ppm [4F, —OCF$_2$CF$_2$CF$_2$CF$_2$O—, —OCF$_2$CF$_2$CF$_2$CH$_2$O—]

As a result of $^{19}$F-NMR, it was found that, in the compound 8, n=3.7.

$^1$H-NMR (solvent: none, reference substance: D$_2$O)
δ=3.0 ppm to 4.4 ppm [24H, HOCH$_2$CH(OH)CH$_2$OCH$_2$CH(OH)CH$_2$OCH$_2$CF$_2$CF$_2$CF$_2$O(CF$_2$CF$_2$CF$_2$CF$_2$O)$_n$CF$_2$CF$_2$CF$_2$CH$_2$OCH$_2$CH(OH)CH$_2$OCH$_2$CH(OH)CH$_2$O H]
δ=4.6 ppm [6H, HOCH$_2$CH(OH)CH$_2$OCH$_2$CH(OH)CH$_2$OCH$_2$CF$_2$CF$_2$CF$_2$O(CF$_2$CF$_2$CF$_2$CF$_2$O)$_n$CF$_2$CF$_2$CF$_2$CH$_2$OCH$_2$CH(OH)CH$_2$OCH$_2$CH(OH)CH$_2$O H]

The resulting compound 8 was used as a lubricant in Example 8.

Example 9

The compound 9, represented by the following formula, was synthesized as below.

HOCH$_2$CHCH$_2$OCH$_2$CF(OCF$_2$CF)$_o$OCF$_2$CF$_2$O(CFCF$_2$O)$_o$CFCH$_2$OCH$_2$CHCH$_2$OCH$_2$CHCH$_2$OH
    |                |       |              |            |       |       |
    OH              CF$_3$   CF$_3$          CF$_3$       CF$_3$   OH      OH

Note that the compound 9 corresponds to a compound represented by formula (1) wherein R$^2$ is constituted by a Krytox skeleton and a C2 skeleton and R$^3$ is a hydrocarbon group represented by —OCH$_2$CH(OH)CH$_2$OH.

The compound 9 was synthesized in the same manner as the compound 1, except that perfluoropolyether to be used was changed to perfluoropolyether represented by HO CH$_2$CF(CF$_3$)(OCF$_2$CF(CF$_3$))$_o$OCF$_2$CF$_2$O(CF(CF$_3$)CF$_2$O)$_o$ CF(CF$_3$)CH$_2$OH. Identification results of the compound 9 by NMR are shown below.

$^{19}$F-NMR (solvent: none, reference: —CF(CF$_3$)CF$_2$O— in the product was regarded as −80.4 ppm)
δ=−144.7 ppm [5F, —CF(CF$_3$)CF$_2$O—]
δ=−134.5 ppm [2F, —OCF(CF$_3$)CH$_2$O—]
δ=−86.0 ppm [4F, —OCF$_2$CF$_2$O—]
δ=−83.1 ppm [11F, —CF(CF$_3$)CF$_2$O—]
δ=−80.4 ppm [22F, —CF(CF$_3$)CF$_2$O—, —OCF(CF$_3$)CH$_2$O—]

As a result of $^{19}$F-NMR, it was found that, in the compound 9, o=2.7.

$^1$H-NMR (solvent: none, reference substance: D$_2$O)
δ=3.0 ppm to 4.4 ppm [19H, HOCH$_2$CH(OH)CH$_2$OCH$_2$CF(CF$_3$)(OCF$_2$CF(CF$_3$))$_o$OCF$_2$CF$_2$O(CF(CF$_3$)CF$_2$O)$_o$CF(CF$_3$)CH$_2$OCH$_2$CH(OH)CH$_2$OCH$_2$CH(OH)CH$_2$OH]
δ=4.6 ppm [5H, HOCH$_2$CH(OH)CH$_2$OCH$_2$CF(CF$_3$)(OCF$_2$CF(CF$_3$))$_o$OCF$_2$CF$_2$O(CF(CF$_3$)CF$_2$O)$_o$CF(CF$_3$)CH$_2$OCH$_2$CH(OH)CH$_2$OCH$_2$CH(OH)CH$_2$OH]

The resulting compound 9 was used as a lubricant in Example 9.

Example 10

The compound 10, represented by the following formula, was synthesized as below.

HOCH$_2$CHCH$_2$OCH$_2$CHCH$_2$OCH$_2$CF(OCF$_2$CF)$_o$OCF$_2$CF$_2$O(CFCF$_2$O)$_o$CFCH$_2$OCH$_2$CHCH$_2$OCH$_2$CHCH$_2$OH
    |             |              |              |        |       |              |              |
    OH           OH              CF$_3$          CF$_3$   CF$_3$   CF$_3$          OH            OH

Note that the compound 10 corresponds to a compound represented by formula (1) wherein R$^2$ is constituted by a Krytox skeleton and a C2 skeleton and R$^3$ is a hydrocarbon group represented by OCH$_2$CH(OH)CH$_2$OCH$_2$CH(OH) CH$_2$OH.

The compound 10 was synthesized in the same manner as the compound 2, except that perfluoropolyether to be used was changed to perfluoropolyether represented by HOCH$_2$CF(CF$_3$)(OCF$_2$CF(CF$_3$))$_o$OCF$_2$CF$_2$O(CF(CF$_3$) CF$_2$O)$_o$CF(CF$_3$)CH$_2$OH. Identification results of the compound 10 by NMR are shown below.

$^{19}$F-NMR (solvent: none, reference: —CF(CF$_3$)CF$_2$O— in the product was regarded as −80.4 ppm)
δ=−144.7 ppm [5F, —CF(CF$_3$)CF$_2$O—]
δ=−134.5 ppm [2F, —OCF(CF$_3$)CH$_2$O—]
δ=−86.0 ppm [4F, —OCF$_2$CF$_2$O—]
δ=−83.1 pm [11F, —CF(CF$_3$)CF$_2$O—]
δ=−80.4 ppm [22F, —CF(CF$_3$)CF$_2$O—, —OCF(CF$_3$)CH$_2$O—]

As a result of $^{19}$F-NMR, it was found that, in the compound 10, o=2.7.

$^1$H-NMR (solvent: none, reference substance: D$_2$O)
δ=3.0 ppm to 4.4 ppm [24H, HOCH$_2$CH(OH)CH$_2$OCH$_2$CH(OH)CH$_2$OCH$_2$CF(CF$_3$)(OCF$_2$CF(CF$_3$))$_o$OCF$_2$CF$_2$O(CF(CF$_3$)CF$_2$O)$_o$CF(CF$_3$)CH$_2$OCH$_2$CH(OH)CH$_2$OCH$_2$CH(OH)CH$_2$OH]
δ=4.6 ppm [6H, HOCH$_2$CH(OH)CH$_2$OCH$_2$CH(OH)CH$_2$OCH$_2$CF(CF$_3$)(OCF$_2$CF(CF$_3$))$_o$CF$_2$CF$_2$O(CF(CF$_3$)CF$_2$O)$_o$CF(CF$_3$) CH$_2$O CH$_2$CH(OH) CH$_2$OCH$_2$CH(OH) CH$_2$OH]

The resulting compound 10 was used as a lubricant in Example 10.

Comparative Example 1

As a lubricant in Comparative Example 1, a compound 11 as below was used. The compound 11 had a Demnum skeleton and four hydroxyl groups in total in hydrocarbon groups at both terminals thereof.

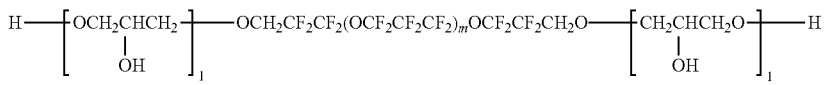

Note, here, that m=6.1.

Comparative Example 2

As a lubricant in Comparative Example 2, a compound 12 as below was used. The compound 12 had a Demnum skeleton and seven hydroxyl groups in total in hydrocarbon groups at both terminals thereof.

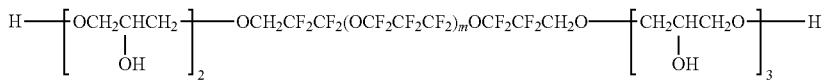

Note, here, that m=5.8.

[Results of Evaluation]

Table 1 shows results of the evaluation of heat resistance by TG, the evaluation of solubility in a fluorine-based solvent, and the evaluation of evaporativity on a magnetic disk.

TABLE 1

| | | Number of hydroxyl groups in molecule | 50% weight reduction temperature (T50) | Solubility in fluorine-based solvent | Thickness reduction rate of lubricant on magnetic disk |
|---|---|---|---|---|---|
| Example 1 | Compound 1 | 5 | Good (292° C.) | Good | Good (8%) |
| Example 2 | Compound 2 | 6 | Good (318° C.) | Good | Good (8%) |
| Example 3 | Compound 3 | 5 | Good (290° C.) | Good | Good (9%) |
| Example 4 | Compound 4 | 6 | Good (316° C.) | Good | Good (9%) |
| Example 5 | Compound 5 | 5 | Good (299° C.) | Good | Good (2%) |
| Example 6 | Compound 6 | 6 | Good (325° C.) | Good | Good (2%) |
| Example 7 | Compound 7 | 5 | Good (296° C.) | Good | Good (7%) |
| Example 8 | Compound 8 | 6 | Good (322° C.) | Good | Good (7%) |
| Example 9 | Compound 9 | 5 | Good (293° C.) | Good | Good (8%) |
| Example 10 | Compound 10 | 6 | Good (317° C.) | Good | Good (8%) |
| Comparative Example 1 | Compound 11 | 4 | Poor (270° C.) | Good | Poor (15%) |
| Comparative Example 2 | Compound 12 | 7 | Good (330° C.) | Poor | *1 |

*1: Since the compound 12 is insoluble in a fluorine-based solvent, it is impossible to apply the compound 12 to a magnetic disk.

As is clear from Table 1, the compounds in Examples 1 to 10 and Comparative Example 2 were each higher than that in Comparative Example 1 in 50% weight reduction temperature (T50).

Further, the compounds in Examples 1 to 10 and Comparative Example 1 each dissolved in a fluorine-based solvent, whereas the compound in Comparative Example 2 was insoluble in a fluorine-based solvent. This shows that the compound in Comparative Example 2 was unusable for application to a magnetic disk.

Moreover, the compounds in Examples 1 to 10 were each lower than that in Comparative Example 1 in thickness reduction rate of a lubricant on a magnetic disk. Thus, the compounds in Examples 1 to 10 were each less likely to decrease in thickness than that in Comparative Example 1 even when placed in a heating environment for a long time.

Namely, the compound in accordance with an embodiment of the present invention has low volatility, i.e., excellent heat resistance and has favorable solubility in a fluorine-based solvent.

INDUSTRIAL APPLICABILITY

A perfluoropolyether compound in accordance with an aspect of the present invention can be suitably used as a lubricant for magnetic disks.

REFERENCE SIGNS LIST

1 Magnetic disk
2 Lubricant layer
3 Protective film layer (protective layer)
4 Recording layer
5 Lower layer
6 Soft magnetic lower layer
7 Adhesive layer
8 Non-magnetic substrate

The invention claimed is:

1. A lubricant comprising:
a perfluoropolyether compound represented by the following formula (1):

$$R^1-CH_2-R^2-CH_2-R^3 \qquad (1)$$

wherein: $R^1$ is $HOCH_2CH(OH)CH_2OCH_2CH(OH)CH_2O-$;
$R^2$ is $-(CF_2)_xO(CF_2CF_2CF_2O)_m(CF_2)_x-$, wherein x is a real number of 1 to 3, m is a real number of 1 to 15; and
$R^3$ is $-OCH_2CH(OH)CH_2OH$ or $-OCH_2CH(OH)CH_2OCH_2CH(OH)CH_2OH$,
wherein at a temperature of 550° C., from heating at a rate of temperature rise of 2° C./min under a nitrogen atmosphere, the lubricant exhibits a 50% weight reduction temperature of higher than 280° C.

2. A magnetic disk comprising:
a recording layer;
a protective layer disposed on the recording layer; and
a lubricant layer disposed on the protective layer,
the lubricant layer containing a perfluoropolyether compound represented by the following formula (1):

$$R^1-CH_2-R^2-CH_2-R^3 \qquad (1)$$

wherein: $R^1$ is $HOCH_2CH(OH)CH_2OCH_2CH(OH)CH_2O-$;
$R^2$ is $-(CF_2)_xO(CF_2CF_2CF_2O)_m(CF_2)_x-$, wherein x is a real number of 1 to 3, m is a real number of 1 to 15; and
$R^3$ is $-OCH_2CH(OH)CH_2OH$ or $-OCH_2CH(OH)CH_2OCH_2CH(OH)CH_2OH$.

3. A lubricant composition comprising: a fluorine-based solvent and a perfluoropolyether compound represented by the following formula (1):

$$R^1-CH_2-R^2-CH_2-R^3 \qquad (1)$$

wherein: $R^1$ is $HOCH_2CH(OH)CH_2OCH_2CH(OH)CH_2O-$;
$R^2$ is $-(CF_2)_xO(CF_2CF_2CF_2O)_m(CF_2)_x-$, wherein x is a real number of 1 to 3, m is a real number of 1 to 15; and
$R^3$ is $-OCH_2CH(OH)CH_2OH$ or $-OCH_2CH(OH)CH_2OCH_2CH(OH)CH_2OH$.

4. The lubricant composition of claim 3, wherein at a temperature of 550° C., from heating at a rate of temperature rise of 2° C./min under a nitrogen atmosphere, the perfluoropolyether compound exhibits a 50% weight reduction temperature of higher than 280° C.

5. A magnetic disk comprising:
a recording layer;
a protective layer disposed on the recording layer; and
a lubricant layer disposed on the protective layer, the lubricant layer containing the lubricant composition recited in claim 3.

* * * * *